(12) United States Patent  (10) Patent No.: US 6,726,709 B1
Lennox  (45) Date of Patent: Apr. 27, 2004

(54) METHOD AND DEVICE FOR REDUCING DEATH AND MORBIDITY FROM STROKE

(75) Inventor: Charles D. Lennox, Hudson, NH (US)

(73) Assignee: MedCool, Inc., Wellesley, MA (US)

( * ) Notice: Subject to any disclaimer, the term of this patent is extended or adjusted under 35 U.S.C. 154(b) by 0 days.

(21) Appl. No.: 10/131,013

(22) Filed: Apr. 24, 2002

Related U.S. Application Data

(60) Provisional application No. 60/287,457, filed on Apr. 30, 2001.

(51) Int. Cl.[7] .................................................. A61F 7/00
(52) U.S. Cl. ........................ 607/105; 607/104; 606/22; 606/23
(58) Field of Search .............................. 606/20, 21, 22, 606/23, 25, 26, 130; 607/104, 105

(56) References Cited

U.S. PATENT DOCUMENTS

| | | | | |
|---|---|---|---|---|
| 3,298,371 A | * | 1/1967 | Lee ................................ 606/23 |
| 3,971,383 A | * | 7/1976 | van Gerven ................... 606/23 |
| 5,139,496 A | * | 8/1992 | Hed ............................... 606/23 |
| 5,577,387 A | * | 11/1996 | Maytal ......................... 62/51.2 |
| 5,620,479 A | | 4/1997 | Diederich ..................... 607/97 |
| 5,649,936 A | * | 7/1997 | Real ............................. 606/130 |
| 5,910,104 A | * | 6/1999 | Dobak et al. ................ 600/121 |
| 5,921,982 A | | 7/1999 | Lesh et al. ..................... 606/41 |
| 6,248,126 B1 | * | 6/2001 | Lesser et al. ................ 607/113 |
| 6,251,105 B1 | * | 6/2001 | Mikus et al. ................. 606/22 |
| 6,272,370 B1 | | 8/2001 | Gillies et al. ............... 600/411 |
| 6,428,531 B1 | | 8/2002 | Visuri et al. ................... 606/7 |
| 6,481,439 B1 | | 11/2002 | Lewis et al. ................ 128/898 |

* cited by examiner

Primary Examiner—Roy D. Gibson
(74) Attorney, Agent, or Firm—Chappin & Huang, L.L.C.; Barry W. Chapin, Esq.

(57) ABSTRACT

Disclosed is an apparatus and method for preventing secondary ischemic injury in the brain. The apparatus includes an interstitial brain-cooling probe that is placed into an ischemic region of the brain by stereotaxic surgical technique, and a control console. The control console provides a source of cooling fluid to the interstitial brain-cooling probe, and controls the flow of cooling fluid according to signals received from a temperature sensor mounted on the interstitial brain-cooling probe. The interstitial brain-cooling probe cools an ischemic region of the brain from within the ischemic region, and cooling is substantially limited to the ischemic region. Cooling is provided for a period of time greater than one hour.

30 Claims, 11 Drawing Sheets

METHOD AND DEVICE FOR REDUCING DEATH AND MORBIDITY FROM STROKE

CROSS REFERENCE TO RELATED APPLICATIONS

This application is entitled to the benefit of Provisional Patent Application Ser. No. 60/287,457 filed Apr. 30, 2001.

BACKGROUND

Field of Invention

This invention relates to a method and device for inducing localized hypothermia in tissue, specifically brain tissue that is at risk of necrosis due to stroke.

BACKGROUND

Description of Prior Art

Stroke is a leading cause of death and disability. It is estimated that over 725,000 people suffer a major stroke in the United States each year, and that over 100,000 of these people die. There are two main categories of stroke: ischemic and hemorrhagic. A blockage in an artery in the brain causes ischemic stroke, and a rupture in an artery in the brain causes hemorrhagic stroke. There are approximately 600,000 ischemic stokes, and 125,000 hemorrhagic strokes in the United States each year.

Within the last decade there has been a marked increase in understanding why and how brain cells die from ischemic stroke. Cells within an infarction zone have dramatically reduced blood flow of 20% of normal or less. Cells within this infarction zone will be irreversibly damaged within a few minutes. Surrounding the infarcted zone is a volume of tissue called the "ischemic penumbra" or "transitional zone" in which blood flow is between 20% and 50% of normal. Cells in this area are endangered, but not irreversibly damaged. Ischemia in the infarction zone, and in the ischemic penumbra causes the ischemic cells to release excitatory proteins which migrate into surrounding tissues triggering a hyper metabolic response that leads to cell death beyond the infarction zone and the ischemic penumbra. This hyper metabolic response triggers inflammation, edema, local and global pyrexia, cerebral hypertension, apoptosis, and an increase in intra-cranial pressure causing a cascade of cell injury and death. This cascade of cell injury and death is referred to as secondary ischemic injury in the literature. Nowhere in the art is a mechanism described to that can effectively prevent or limit the migration of excitatory proteins from ischemic tissue, to surrounding normal tissue in the brain.

There is a growing body of research that shows that hypothermia is neuroprotective, however, the exact mechanisms are not fully understood. Schwab et al recently demonstrated that inducing systemic hypothermia following severe ischemic stroke provides a significant improvement in clinical outcome. Schwab treated 25 patients suffering from hemispheric stroke as a result of infarction of the middle cerebral artery with systemic hypothermia at 33 degrees centigrade for 48 to 72 hours. All patients were under full anesthesia during the period of hypothermia. The survival rate, and the clinical outcome of the survivors was significantly better than would otherwise have been expected. Schwab also demonstrated that critical elevations in intra-cranial pressure could be effectively reduced by systemic hypothermia following ischemic stroke.

However, there was a significant complication rate, unrelated to the stroke, but due to the depth and duration of systemic hypothermia Also, it took 3.5 to 6.2 hours for the body core temperature to reach the target therapeutic temperature of 33 degrees centigrade, and it took an average of 18 hours for the body temperature to return to normal after systemic cooling was withdrawn. All of the patients that died in this study did so as a result of a terminal rise in intra-cranial pressure during the rewarming period. Schwab notes, "Rewarming has to be considered the critical phase of hypothermia therapy".

Kammersgaard et al recently reported treating 17 patients suffering ischemic stroke with systemic hypothermia for 6 hours upon admission of the patient to the hospital. Unlike in the Schwab study, there was no body core temperature target; the patient was cooled by "forced cold air method" for 6 hours and the core body temperature was monitored. At six hours the average core body temperature was 36.5 degrees centigrade. Kammersgaard reported that the hypothermia therapy was well tolerated by the patients, and did not require anesthesia. Also, there were no complications encountered due to the hypothermia therapy. However, the clinical outcome of patients studied showed no statically significant improvement in outcome over the historical controls used in this study.

Systemic hypothermia has historically been accomplished by immersion of the patient's body in a cool bath. Today there are several commercial systemic hypothermia systems available. They consist of blankets or pads where cooled water is circulated through channels in the walls of the blanket or pad, and the patient's body is maintained in intimate contact. Medivan Corp. manufactures an example of a modern hypothermia system under the trade name Arctic Sun Cooling System.

Systemic hypothermia has been demonstrated to be effective in improving the outcome of ischemic stroke, however, there are several drawbacks to this approach: 1) It takes several hours to lower a patient's body to therapeutic temperatures. This delay in achieving therapeutic temperatures allows for the progression of irreversible injury to the brain. 2) The practical therapeutic hypothermic temperature and duration is limited by the ability of the patient to tolerate, or survive the therapy. 3) The side effects of systemic hypothermia are frequent and can be life threatening, especially in frail patients. Side effects include shivering, cardiac arrhythmia and arrest, pneumonia, infections, and coagulation disorders. 4) The target of hypothermia therapy is the zone around the cerebral infarction, therefore inducing hypothermia systemically places the patient at undue risk. 5) During the "critical phase" (rewarming period) of hypothermia treatment, there is no effective way to manage a sudden and critical increase in intra-cranial pressure, since re-cooling the body to reverse the increase in intra-cranial pressure takes several hours. 6) Brain tissue in a zone of infarction, and in the transitional zone surrounding the infarction have substantially reduced blood perfusion rates, and brain tissues in a zone of infarction, and in the transitional zone surrounding the infarction are in a hyper-metabolic state, therefore heat generated by the hyper-metabolic processes inside the zone of infarction, and inside the transitional zone cannot be effectively dissipated by blood perfusion. This results in a temperature differential between the infarcted and transitional zone, and the surrounding normal tissue, where tissues in the infarcted and transitional zone are at a higher temperature than the surrounding normal tissue. Systemic hypothermia cools a zone of infarction and surrounding transitional zone from without, and therefore cannot eliminate this temperature differential.

There are several examples in the art where catheters are constructed with a cooling means which is placed into the carotid artery to cool the blood entering the head. This offers an advantage over systemic hypothermia, since it provides a means to cool the head to lower temperatures than the rest of the body, but it still results in systemic hypothermia. Also, since the scientific evidence suggests that hypothermia must be maintained for extended periods of time, there is a great risk that clots will form on the catheters and migrate into the brain leading to further episodes of stroke. The mechanism of cooling a zone of infarction in the brain, or the surrounding transitional zone with this approach is the same as with systemic hypothermia, and does not overcome the significant limitations as described above.

There are numerous examples of interstitial cooling probes in the art. Nowhere in the art is it suggested that interstitial cooling probes may be used to treat stroke, and nowhere in the art is there an example of a cooling probe that may be practically fixated to the head and left indwelling in the brain for the extended periods of time required for effective hypothermia treatment of stroke.

SUMMARY

Therefore, it is an object of this invention to provide a method and apparatus for treating stroke. Another object of this invention is to provide a method and apparatus for treating ischemic stroke. A further object of this invention is to provide a means of reducing secondary ischemic injury in the brain following stroke.

In accordance with one aspect of this invention, stroke is treated by placement of an interstitial cooling probe in the brain, and then cooling the brain with the probe. In another aspect of this invention, stroke is treated by placement of an interstitial cooling probe in to a specific volume of brain tissue that is suffering ischemia due to stroke, and then cooling the ischemic volume of brain tissue with the probe, while otherwise maintaining normal body temperature in unaffected areas of the brain and the body. In accordance with another aspect of this invention, stroke is treated by placement of an interstitial cooling probe into an infarcted volume of brain tissue, then using the probe to cool the infarcted volume of tissue sufficiently to conduct heat from tissue surrounding the infarction into the infarction, thereby cooling the tissue surrounding the infarction. In accordance with another aspect of this invention, stroke is treated by placement of an interstitial cooling probe into an infarcted volume of brain tissue, then using the probe to freeze at least a portion of the infarcted volume of tissue, thereby arresting and/or retarding the migration of excitatory cellular protein from the infarcted volume, to brain tissues surrounding the infarcted volume for a period of time between one hour and one month. In accordance with another aspect of this invention, stroke is treated by placement of an interstitial cooling probe into an infarcted volume of brain tissue, then using the probe to freeze at least a portion of the infarcted volume of tissue thereby arresting and/or retarding the migration of excitatory cellular protein from the infarcted volume, to brain tissues surrounding the infarcted volume for a period of time sufficient for the innate healing response to surround and seal the infarcted volume by fibrosis. In accordance with another aspect of this invention, stroke is treated by placement of an interstitial cooling probe into an infarcted volume of brain tissue, then using the probe to cool the infarcted volume of tissue sufficiently to reduce the metabolic activity in tissue surrounding the infarcted volume. In accordance with another aspect of this invention, stroke is treated by placement of an interstitial cooling probe into an infarcted volume of brain tissue, and then cooling the infarcted volume of brain tissue to a predetermined temperature for a predetermined time. In accordance with another aspect of this invention, stroke is treated by placement of an interstitial cooling probe into an infarcted volume of brain tissue, and then cooling the infarcted volume of brain tissue to a predetermined temperature, where then the temperature is increased gradually over a period of time from the initial low temperature, to normal body temperature, with the period of time being greater than one hour and less than one month. In accordance with another aspect of this invention, stroke is treated by placement of an interstitial cooling probe into an infarcted volume of brain tissue, and then cooling the infarcted volume of brain tissue to a degree based on the physiological response to said cooling. In accordance with another aspect of this invention, apparatus for treating stroke includes an interstitial cooling probe constructed for placement into the brain by stereotaxic radiological guidance, where the distal tip of the probe includes a cooling mechanism with sufficient heat absorbing capability to cool a volume of brain tissue to the degree, and for a period of time sufficient to mitigate the effects of stroke. In another aspect of this invention, apparatus for treating stroke is an interstitial cooling probe where the distal end of the probe contains a mechanism for cooling tissue surrounding the distal tip of the probe, and a mechanism near the distal tip to sense an effect of said cooling. In another aspect of this invention, apparatus for treating stroke is an interstitial cooling probe constructed for an extended period of cooling and indwelling in the brain, with the period of cooling and indwelling being greater than one hour, and as long as one month.

OBJECTS AND ADVANTAGES

Accordingly, besides the objects and advantages of the method and apparatus to treat stroke described in my patent above, several objects and advantages of the present invention are:

(a) to provide localized hypothermia to a volume of brain tissue at risk from stroke to the degree that offers maximum clinical benefit without inducing a hypothermia in areas of the brain or the body that are not at risk from stroke;

(b) to provide localized hypothermia to a volume of brain tissue surrounding a zone of infarction by removing heat from about the center of the infarction to a sufficient degree that the volume of tissue surrounding the infarction is cooled to the degree that has maximal clinical benefit;

(c) to provide localized hypothermia to a volume of brain tissue at risk from stroke where the method for inducing hypothermia takes advantage of the fact that tissue about the center of an infarction lacks perfusion, therefore providing an optimal medium for conducting heat from surrounding tissue.

(d) to provide localized hypothermia to a volume of brain tissue at risk from stroke where the method for inducing hypothermia takes advantage of the fact that tissue about the center of an infarction is dead or irreversibly injured, therefore providing a volume of tissue where otherwise lethal (to brain tissue) hypothermic temperatures (below 0 degrees centigrade) can be achieved without clinical consequence, allowing for a large volume of tissue to be cooled to clinically beneficial temperatures with a single small caliber cooling probe;

(e) to provide localized hypothermia to a volume of brain tissue at risk from stroke where the method for inducing hypothermia inherently produces a temperature profile in the volume of brain tissue at risk from stroke where tissues with lower blood perfusion rates are cooled to lower temperatures than tissues with higher blood perfusion rates; where tissues with lower blood perfusion rates are at greater risk of irreversible injury than tissue with higher blood perfusion rates, and where the neuroprotective effects of hypothermia increases as tissue temperature decreases, therefore providing greatest neuroprotective effects from hypothermia to brain tissues at greatest risk;

(f) to provide localized hypothermia to a volume of brain tissue at risk from stroke within a minimal time after patient presentation where therapeutic temperatures are achieved rapidly due to the fact that only the affected volume of the brain is cooled, and that the cooling probe may attain temperatures that are otherwise lethal to brain tissue (below 0 degrees centigrade) without clinical consequence;

(g) to provide localized hypothermia to a volume of brain tissue at risk from stroke where the degree of hypothermia is adjusted according to the physiological response to hypothermia, where the physiological response to hypothermia is a change in intra-cranial pressure;

(h) to provide localized hypothermia to a volume of brain tissue at risk from stroke where the degree of hypothermia is adjusted according to the physiological response to hypothermia, where the physiological response to hypothermia is a change in patient symptoms.

(i) to provide localized hypothermia to a volume of brain tissue at risk from stroke where the degree of hypothermia is adjusted according to the physiological response to hypothermia, where the physiological response to hypothermia is a change in localized blood perfusion;

(j) to provide localized hypothermia to a volume of brain tissue at risk from stroke where the degree of hypothermia is adjusted according to the physiological response to hypothermia, where the physiological response to hypothermia is a change in the size of the volume of infarcted tissue;

(k) to provide localized hypothermia to a volume of brain tissue at risk from stroke where the degree of hypothermia is adjusted according to the physiological response to hypothermia, where the physiological response to hypothermia is a change in blood chemistry.

(l) to provide apparatus for inducing localized hypothermia to a volume of brain tissue at risk from stroke according to the objectives stated above;

(m) to provide an interstitial brain cooling probe that is constructed to provide a cooling means at the distal tip;

(n) to provide an interstitial brain cooling probe that is constructed to be placed by stereotaxic radiological guidance by well known surgical methods;

(o) to provide an interstitial brain cooling probe that is constructed to provide for long term cooling and indwelling;

(p) to provide an interstitial brain cooling probe that is constructed to provide for fixation to the head of the patient;

(q) to provide an interstitial brain cooling probe that is constructed to provide for protection against infection;

(r) to provide an interstitial brain cooling probe that is constructed to provide for a means to sense a response to cooling;

(s) to provide an interstitial brain cooling probe that is constructed to provide for a means to control the degree of cooling applied to the surrounding brain tissue;

(t) to provide a system that includes an interstitial brain cooling probe, a control consol, and a means to connect the interstitial brain cooling probe to the control console.

DRAWING FIGURES

FIG. 5 shows the distal end of the interstitial brain-cooling probe with a physiological sensor mounted on the probe.

DESCRIPTION

Figure 1:
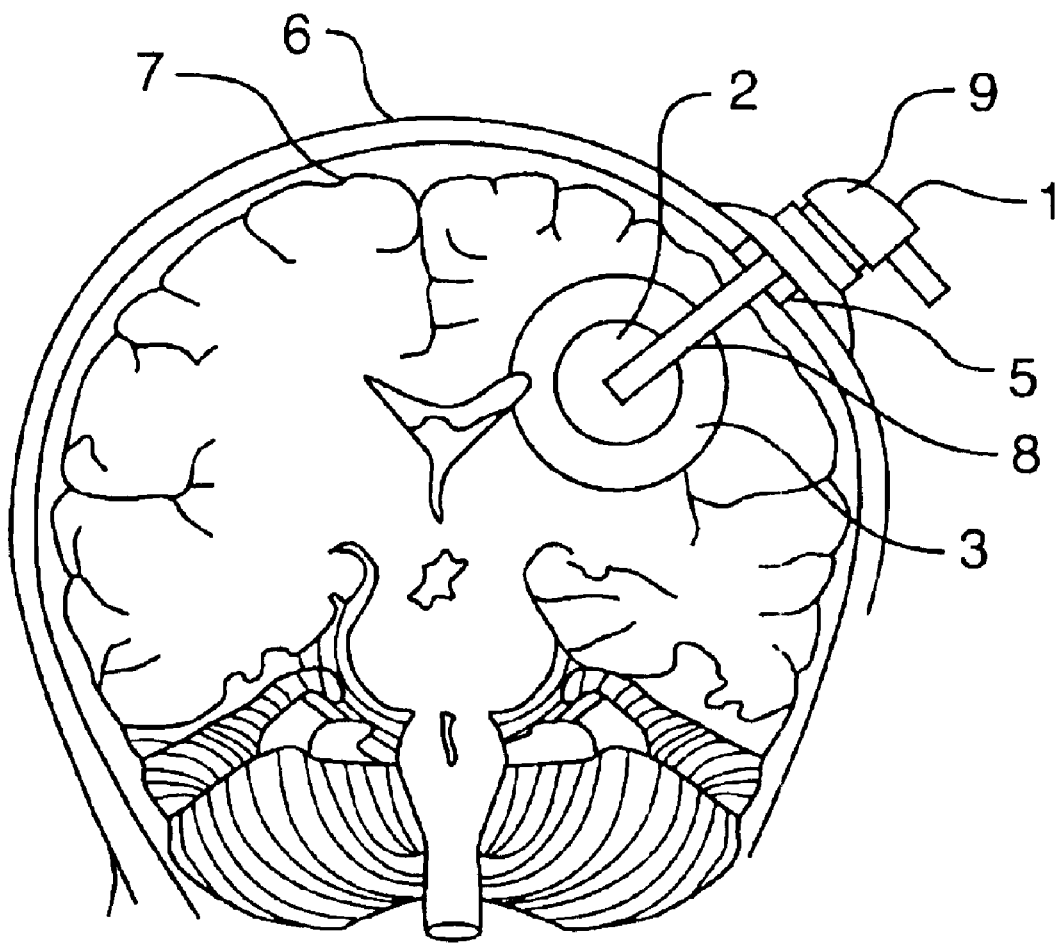
FIG. 1 shows a coronal section of a human brain with the interstitial brain cooling probe fixated to the head, and the distal tip placed in a zone of infarction.
Figure 2:
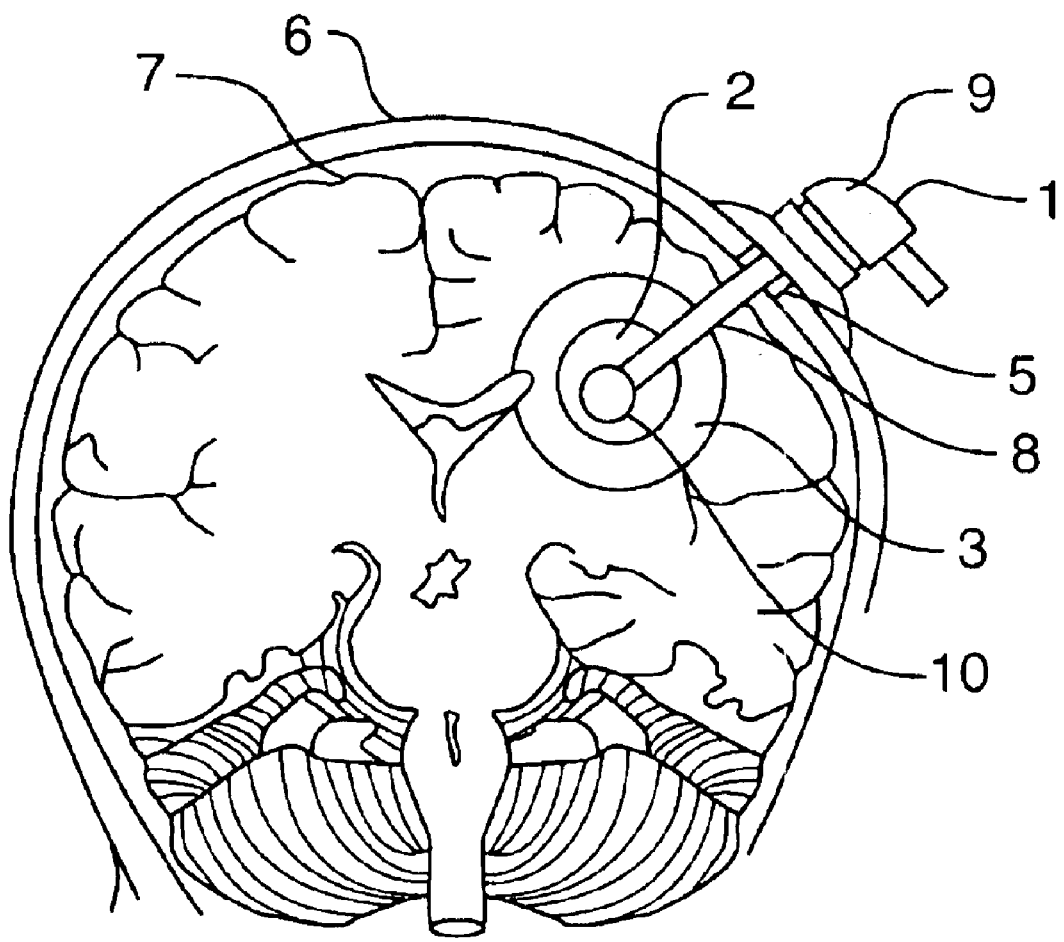
FIG. 2 shows the same view as FIG. 1 with an ice ball formed at the tip of the interstitial brain-cooling probe.
Figure 4:
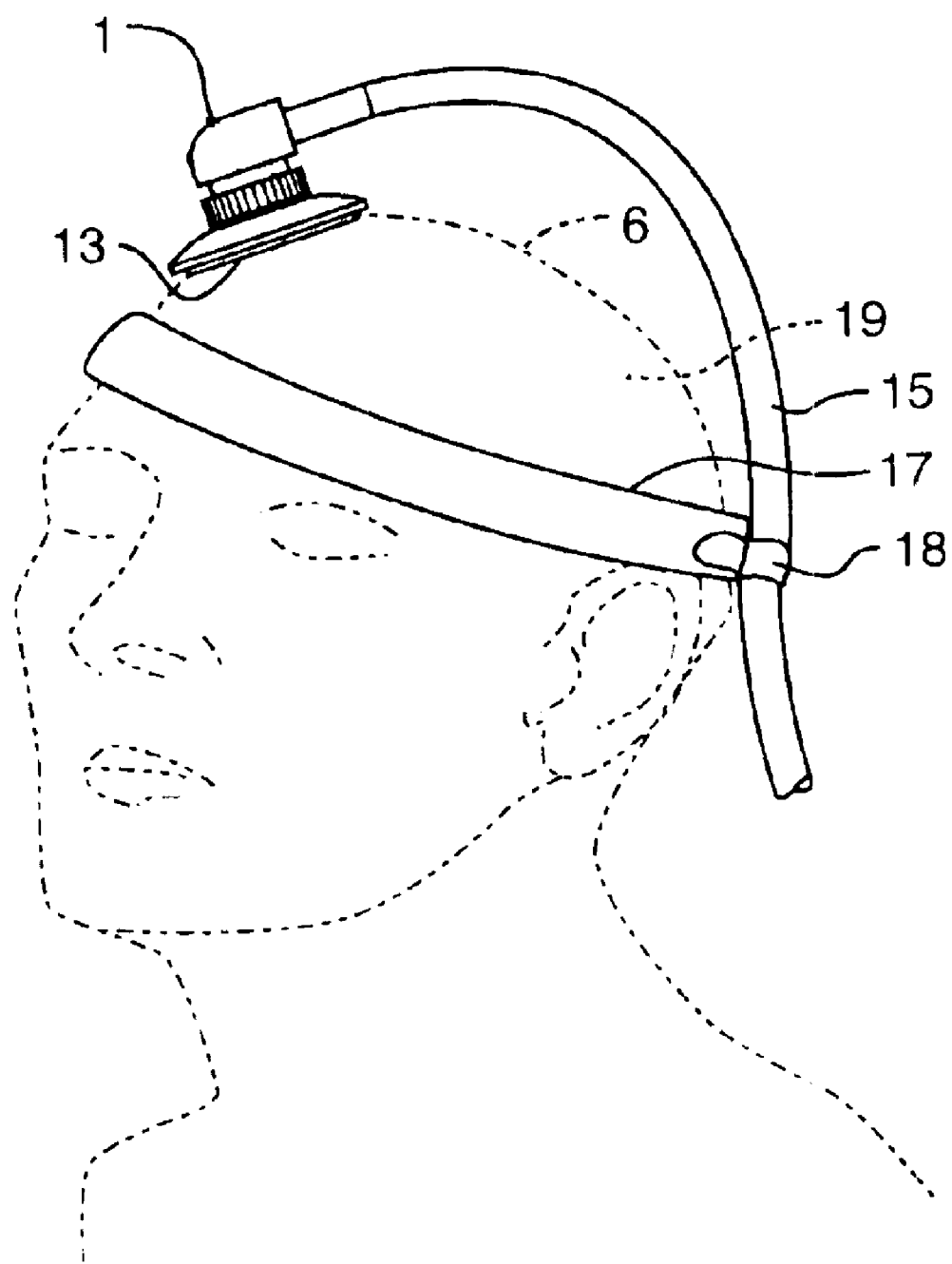
FIG. 4 shows the interstitial brain-cooling probe mounted on a patient's head and a headband for restraining the umbilical that connects the probe to the console.

FIGS. 1, 2, & 4 Preferred Operational Embodiments

FIG. 1 depicts, in simplified form, a coronal section of the head with an interstitial brain cooling probe 1 mounted on the head 6 with the distal cooling end of the probe 4 centered in an infarcted zone of tissue 2. It will be recognized that infarctions of the brain may be nearly spherical as depicted, but are usually irregular in shape. However, this invention can be understood by referring to the simplified representation in the figures. The shaft of the probe 8 connects the distal end of the probe 4 to the proximal end of the probe 9 and passes through a surgically created hole in the skull 5. The probel is activated to cool the region surrounding the infarcted zone of tissue 3 to a temperature below 37 degrees for a period of time between 1 hour and one month. The cooling process is by heat conduction from the region surrounding the infarcted zone 3, through the infarcted zone 2, and into the distal tip of the probe 4. The temperature at the surface of the distal tip of the probe 4 determines the heat removal capacity of the cooling probe. Since the tissue in the infarcted zone 2 is not viable, the temperature at the distal tip of the probe 4, and in the infarcted zone 2 may be maintained at temperatures below 0 degrees centigrade as required to cool the region surrounding the infarcted zone 3 to a temperature range of above 0 degrees centigrade to below 37 degrees centigrade (normal body temperature).

FIG. 2 depicts the same coronal section of the head as in FIG. 1. FIG. 2 shows an "ice ball" 10 that has formed at the distal tip of the probe 4 after thermal equilibrium following activation of the probe 1. The ice ball 10 formation is a result of the surface temperature at the distal tip of the probe 4 being significantly below 0 degrees centigrade in the range of minus 10 to minus 40 degrees centigrade. The ice ball 10 represents a volume of tissue that is at a temperature below 0 degrees centigrade, and is in a solid phase precluding convective transport of cellular proteins. The surface of the ice ball 10 represents an isotherm at 0 degrees centigrade. The ice ball 10 is readily visible by radiological and ultrasonic imaging techniques. Since the geometry of the ice ball 10 can be readily determined by imaging means, and the temperature at the surface of the ice ball 10 is known, computer generated heat transfer algorithms may be used to predict the temperature profile in tissue surrounding the ice ball 10, and this information may be displayed graphically on a computer screen in combination with radiological images of the brain as a means of determining the appropriate temperature that the distal tip of the probe 4 be maintained at to produce optimal clinical benefit.

DESCRIPTION

FIGS. 3, 5–10 Preferred Construction Embodiments

Figure 3:
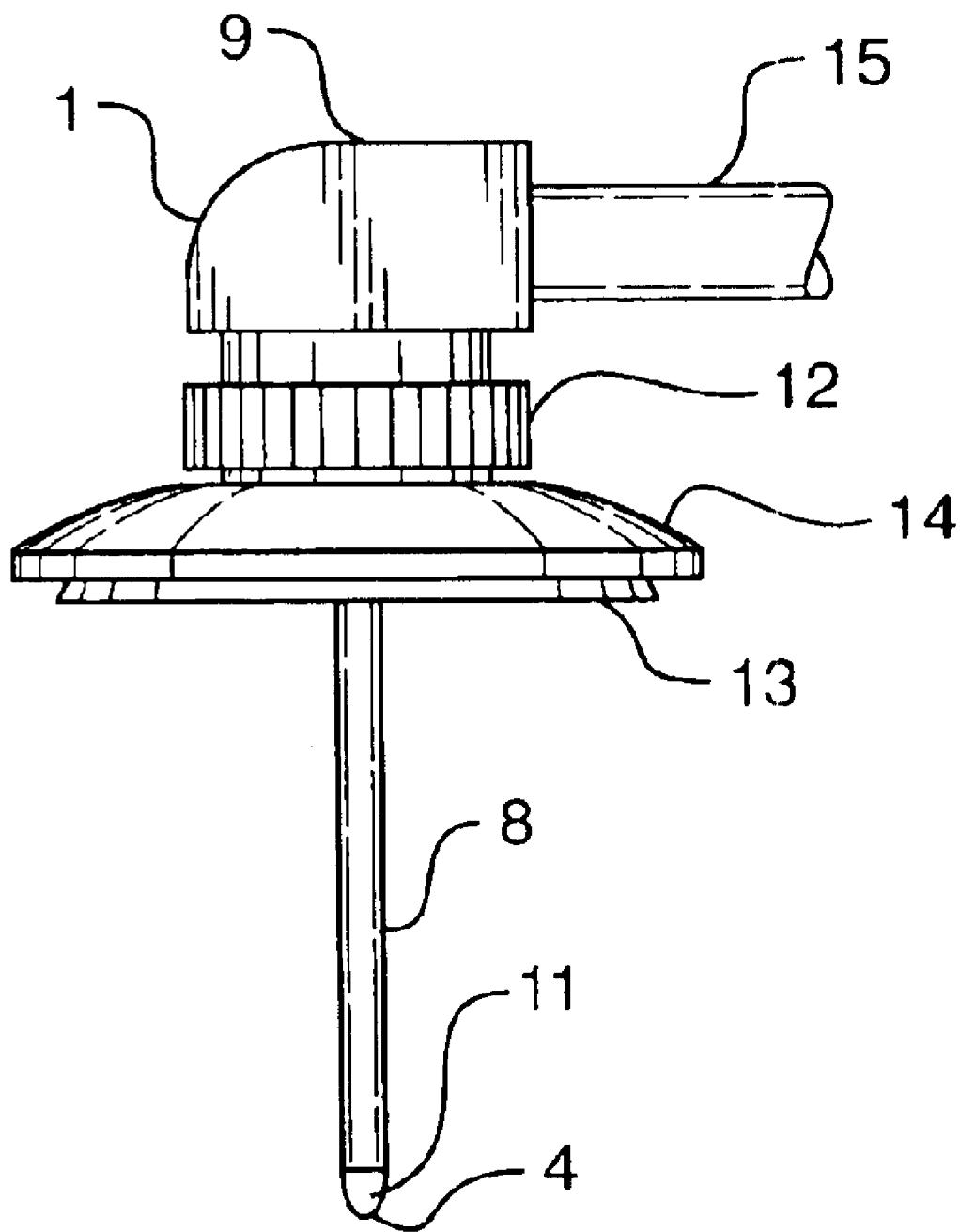
FIG. 3 shows the interstitial brain-cooling probe.

FIG. 3 depicts one embodiment of the interstitial brain-cooling probe 1. The probe 1 consists of a distal end 4 and a proximal end 9. Between the distal end 4, and the proximal end 9 is the probe shaft 8. The diameter of the shaft 8 is between 2 mm and 5 mm. The length of the probe is determined by the specific clinical indication presented. It is envisioned that the probe length will be manufactured and supplied in incremental lengths between 2 cm long to 10 cm long in 2 cm increments. The cooling zone 11 at the distal end is between 0.5 cm and 1.5 cm long about the circumference of the distal end 4. The proximal end of the probe 9 is fixated to the head 6 (FIG. 4). The depth of the probe from the scalp into the brain is adjustable within +/−1 cm by the depth adjustment collar 12. The proximal housing 14 is constructed so that the umbilical cable 15 enters at about 90 degrees to the axis of the probe shaft 8 (FIGS. 3 & 4). The umbilical cable 15 is fixated to the head 19 by a headband 17 and a retaining clip 18 (FIG. 4).

Figure 5:
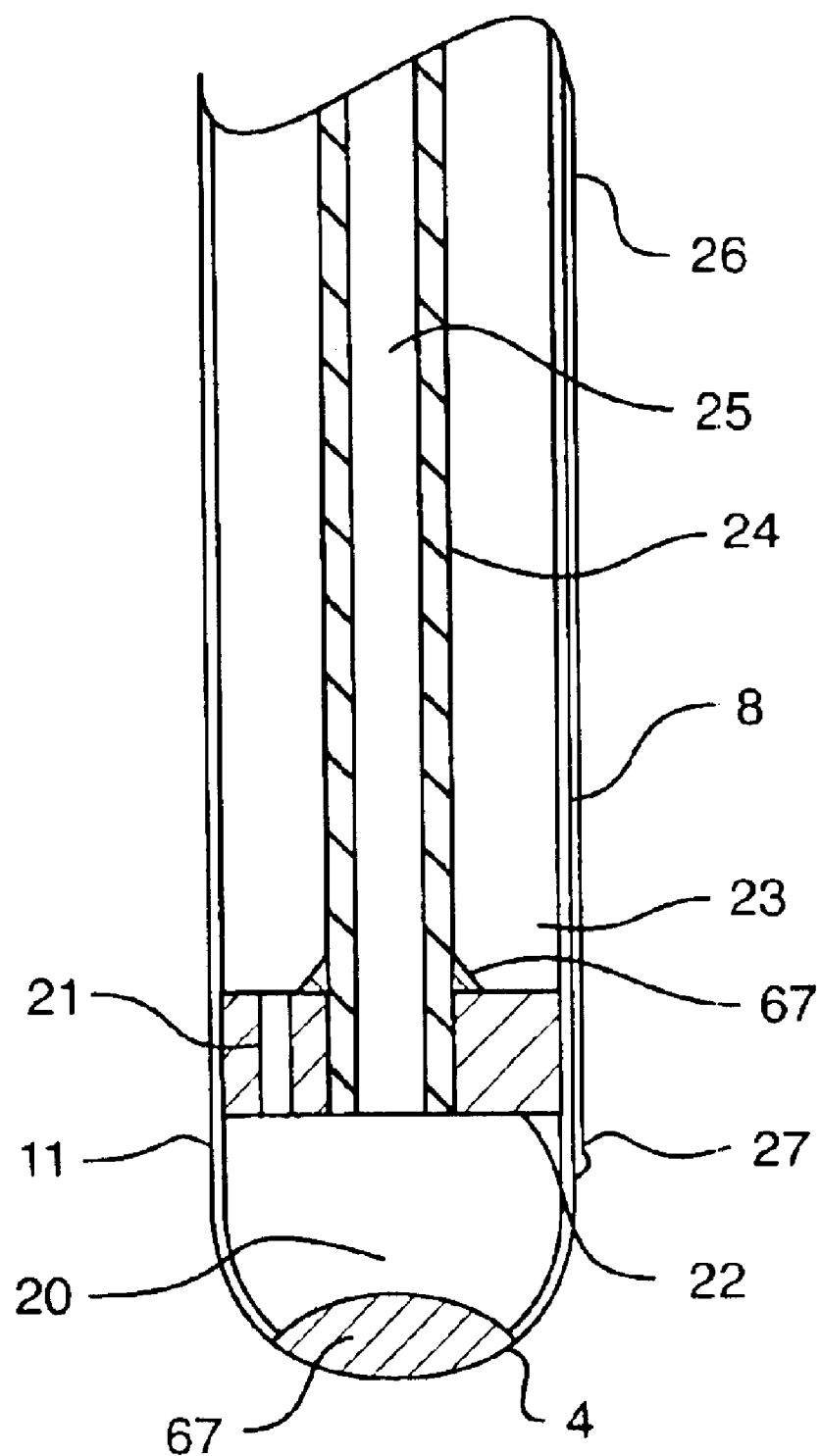
FIG. 5 shows a sectional view of the distal end of the interstitial brain-cooling probe.

FIG. 5 depicts one embodiment of the cooling mechanism. The preferred cooling mechanism is by Joule-Thompson effect where gas at high pressure is expanded through a restriction 21 to an expansion chamber 20 at low pressure. The expansion causes the gas to loose heat causing a reduction in temperature of the gas, and significant cooling of the walls of the expansion chamber 11. Gas is supplied at high pressure from the control console through high pressure tube 36 (FIG. 8) contained in the umbilical cable 15 into the high pressure chamber 23 in the probe shaft 8. The gas at high pressure is metered into the expansion chamber 20, which is at low pressure through a restriction 21 in the pressure bulkhead 22. Gas is exhausted from the expansion chamber through low-pressure tube 24 to the atmosphere. The preferred gasses are nitrogen, or argon, or a mix of argon and nitrogen due to their thermodynamic properties, and their inertness. The pressure of the gas supplied to the tip is between 800 psi and 2500 psi. In addition to the cooling mechanism described above, FIG. 5 shows a thermocouple 27 mounted on the exterior surface of the expansion chamber. The leads of the thermocouple 26 are bonded to the probe shaft 8 with adhesive, and extend into the proximal housing of the probe 9 and through the umbilical cable 15 and are connected to circuitry in the control console 46. The shaft 8 and expansion chamber 20 are formed by a type 304 stainless steel tube with an outside diameter between 3 mm and 5 mm, and a wall thickness of 0.002 inches to 0.004 inches. The expansion chamber 20 is formed from shaft 8 by a common forging process called swaging. The tip of the expansion chamber is closed by silver solder 67. The probe tip 4 is than ground and polished to provide a smooth spherical end. The low-pressure tube 24 is made of type 304 stainless steel and is between 1.5 mm and 2.5 mm in diameter with a wall thickness of about 0.002 inches. The pressure bulkhead 22 is machined from type 304 stainless steel and is attached to the low pressure tube by silver solder 67. The restriction 21 is between 0.002 and 0.008 inches in diameter and is accomplished by electron discharge machining commonly know as EDM. The pressure bulkhead is press fit into the shaft 8 after the low-pressure tube 24 is attached to the pressure bulkhead 22, and before the expansion chamber 20 if formed and sealed.

Figure 6:
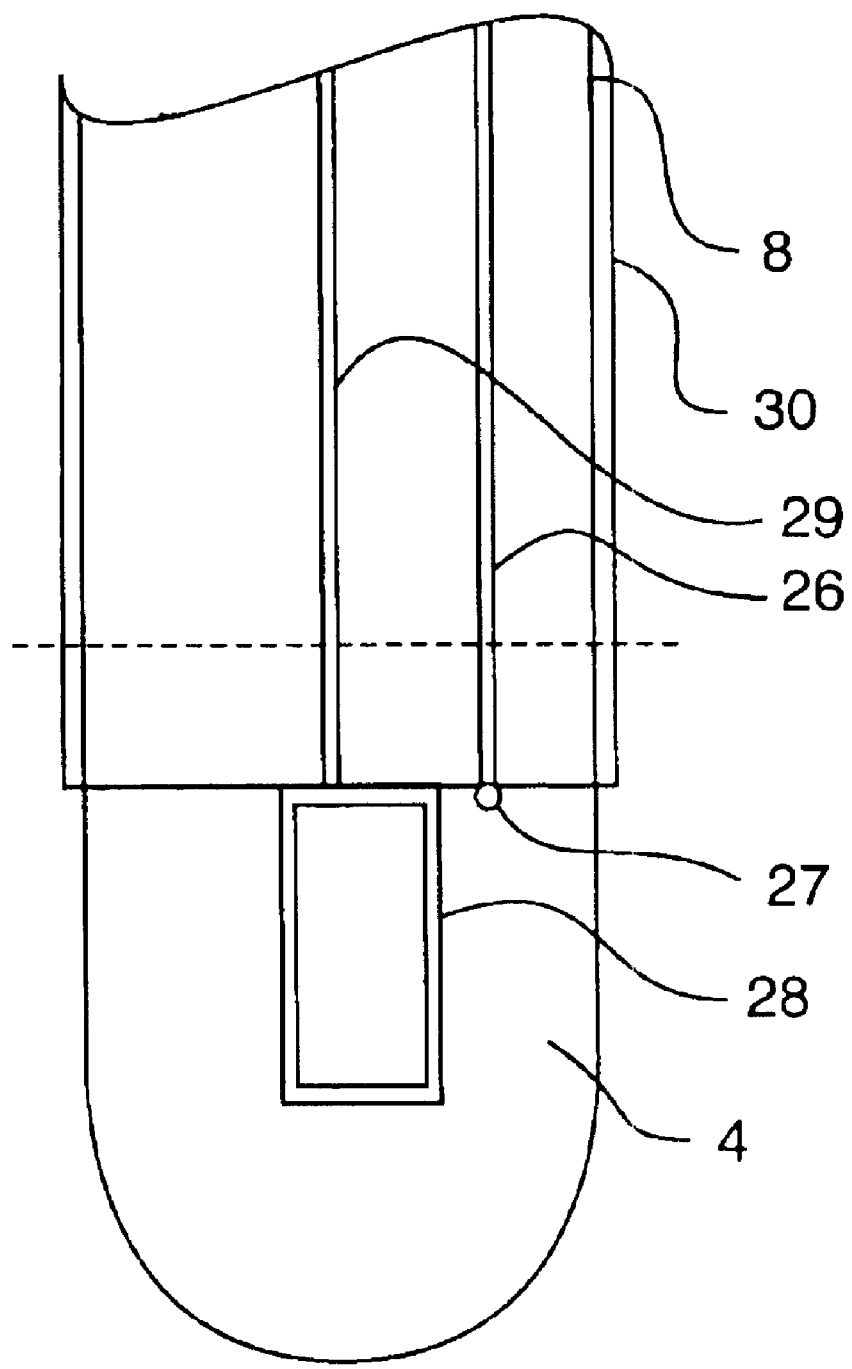
FIG. 6 shows the control console.

FIG. 6 depicts one embodiment of the probe 1 which incorporates at least one ultrasound transducer 28 at the distal end 4 in addition to a thermocouple 27. The ultrasound transducer 28 is used to detect the presence of ice formation at the distal tip by sending acoustic pulses from the transducer and receiving return pulses reflected by the edge of the ice ball 10 (FIG. 2). Information received from the ultrasound transducer is processed by control circuitry in the control console 46 to provide a visual readout on the control console 46 indicative of the presence and size of an ice ball 10, and predictive information regarding the spatial temperature distribution in the tissue surrounding the ice ball 3 & 4. An array of ultrasound transducers may be placed around the circumference of the distal end of the probe 4 to form a sectional image of the ice ball 10 (FIG. 2) by means well known in the art of ultrasound imaging.

Figure 7:
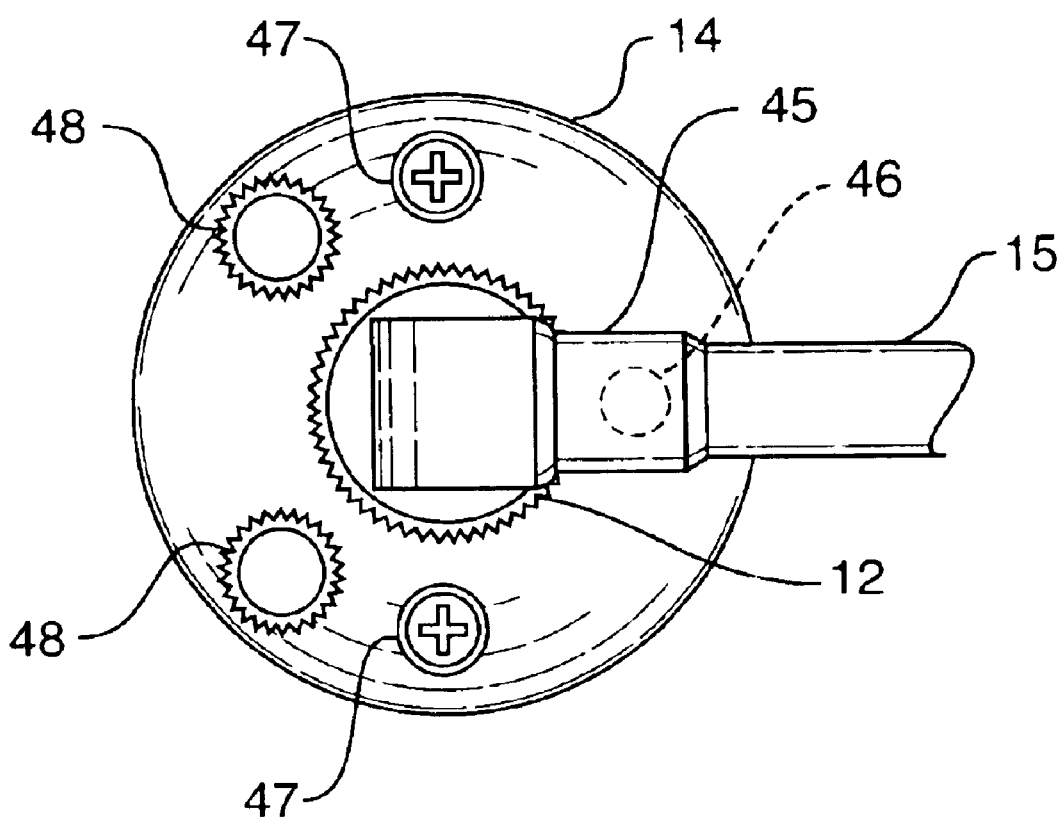
FIG. 7 shows top view of the interstitial brain-cooling probe depicting the preferred method of fixating the probe to the head.

FIG. 7 depicts the preferred mechanism for mounting the interstitial brain-cooling probe to the head. An adjustable tripod on the side of the proximal housing 14 that contacts the head, formed by stationary pod 46, and two vertically adjustable pods 48 provide the alignment to the skull. The probe is fixated to the skull by two screws 47. An open cell foam, saturated with antiseptic fluid 13 (FIGS. 3, 4 & 8) is compressed between the scalp 6 (FIGS. 1, & 4), and the base of the probe housing 14 (FIG. 3), by tightening the two screws 47. The foam 13 and antiseptic fluid protects the craniotomy (hole in the skull), and the screw holes in the skull from infection. Iodine solution marketed under the brand name Betadine® may be used as the antiseptic fluid.

Figure 8:
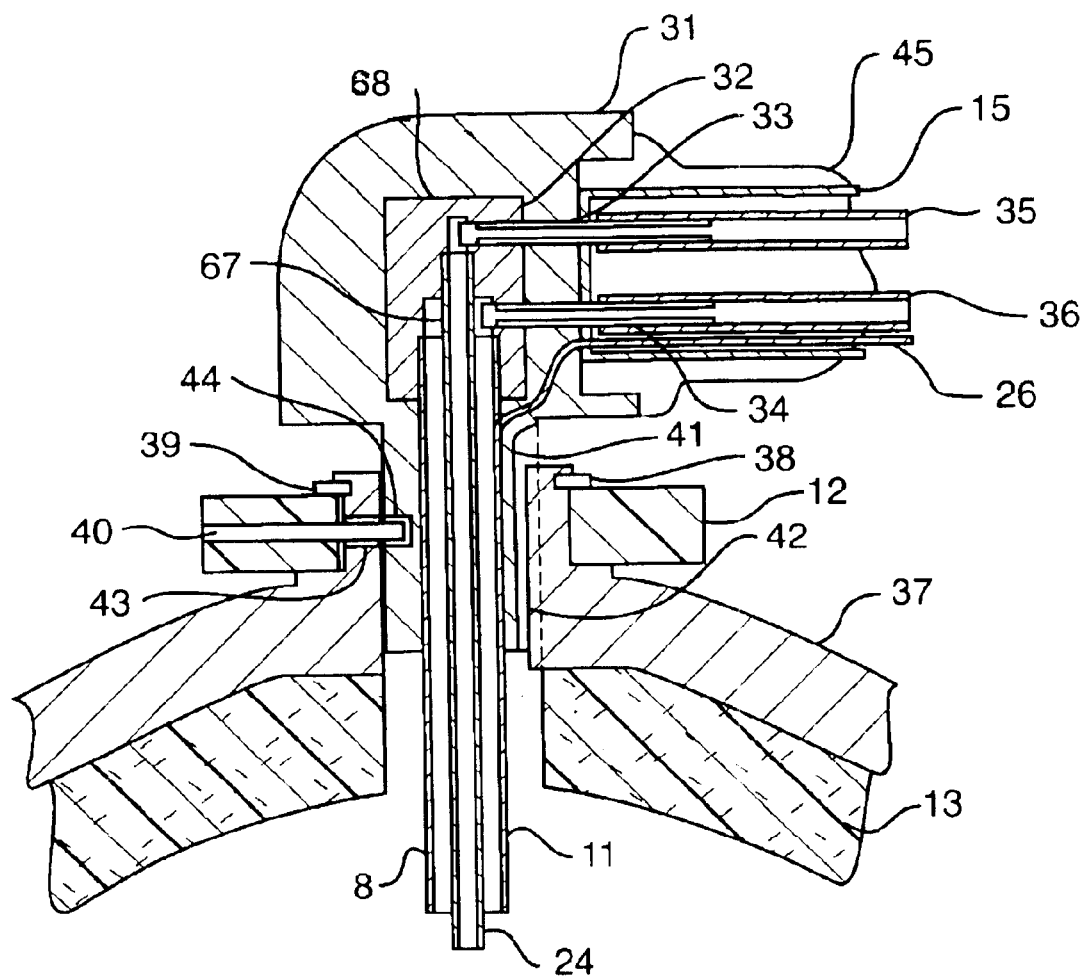
FIG. 8 shows a sectional view of the proximal end of the interstitial brain-cooling probe.

FIG. 8 depicts a sectional assembly view of the proximal end 9 (FIG. 3) of the interstitial brain-cooling probe. The proximal assembly consists of: probe assembly 68, base housing 37, foam pad 13, height adjustment collar 12, probe head 31, height adjustment cam 40, stain relief 45, umbilical cable tube 15, high pressure tube 36, low pressure tube 35, and height adjustment retaining ring 38. Probe assembly 68 consists of: manifold 32, low pressure port tube 33, high pressure port tube 34, probe shaft 8, low pressure tube 24, pressure bulkhead 22 (FIG. 5), thermocouple 27 (FIG. 5), thermocouple lead 26, and silver solder 67. The probe assembly is completed after the assembly of the shaft 8, pressure bulkhead, and low-pressure tube are assembled and the distal tip if formed as described above. The manifold is machined from type 304 stainless steel and soldered to the shaft 8 and low-pressure tube 24 as shown. Low-pressure port tube 35, and high-pressure port tube 36 are soldered to the manifold 32 as shown. Low pressure port tube 33, and high pressure port tube 34 are formed from type 034 stainless steel, and are about 4 mm in diameter, with a wall thickness of 0.003 to 0.005 inches. Both low-pressure port tube 33, and high-pressure port tube 34 may have one or more barb(s) formed by a forging process at the end protruding from the manifold 32 to retain gas tubes 35, and 36. After the probe assembly is complete, probe head 31 is formed around the proximal end of probe assembly 68 by insert molding process. Probe head 31 may be molded from an injection moldable polycarbonate or nylon compound that is suitable for this application. Base housing 37 is formed by injection molding of polycarbonate or nylon. Strain relief 45 is a molded or cast elastomer. Height adjustment ring 12 is injection molded from polycarbonate or nylon. Cam pin 40 is machined from Type 304 stainless steel. Retaining ring 38 is made of stainless steel and is of a common commercially available design. Foam pad 13 is cast with open cell polyurethane foam with a durometer value between 10 and 30. Low pressure tube 35, and high pressure tube 36 are made of flexible nylon and are sized to securely mate with low-pressure port tube 33, and high-pressure port tube 34 respectively. Probe depth adjustment is accomplished by cam 40 assembled integrally to height adjustment ring 12 which is actuated in a radial plane while the cam travels through the spiral cam way 44 formed in probe head 31 during or after the molding process. Cam 40, and height adjustment ring 12 are constrained to radial plane movement by retaining ring 38, and the lower housing 37 as shown. Probe head 31 is constrained to vertical movement by key way 41 formed in probe head 31 during or after the molding process, and by key 42 formed in the lower housing 37 during the molding process as shown.

Figure 9A:
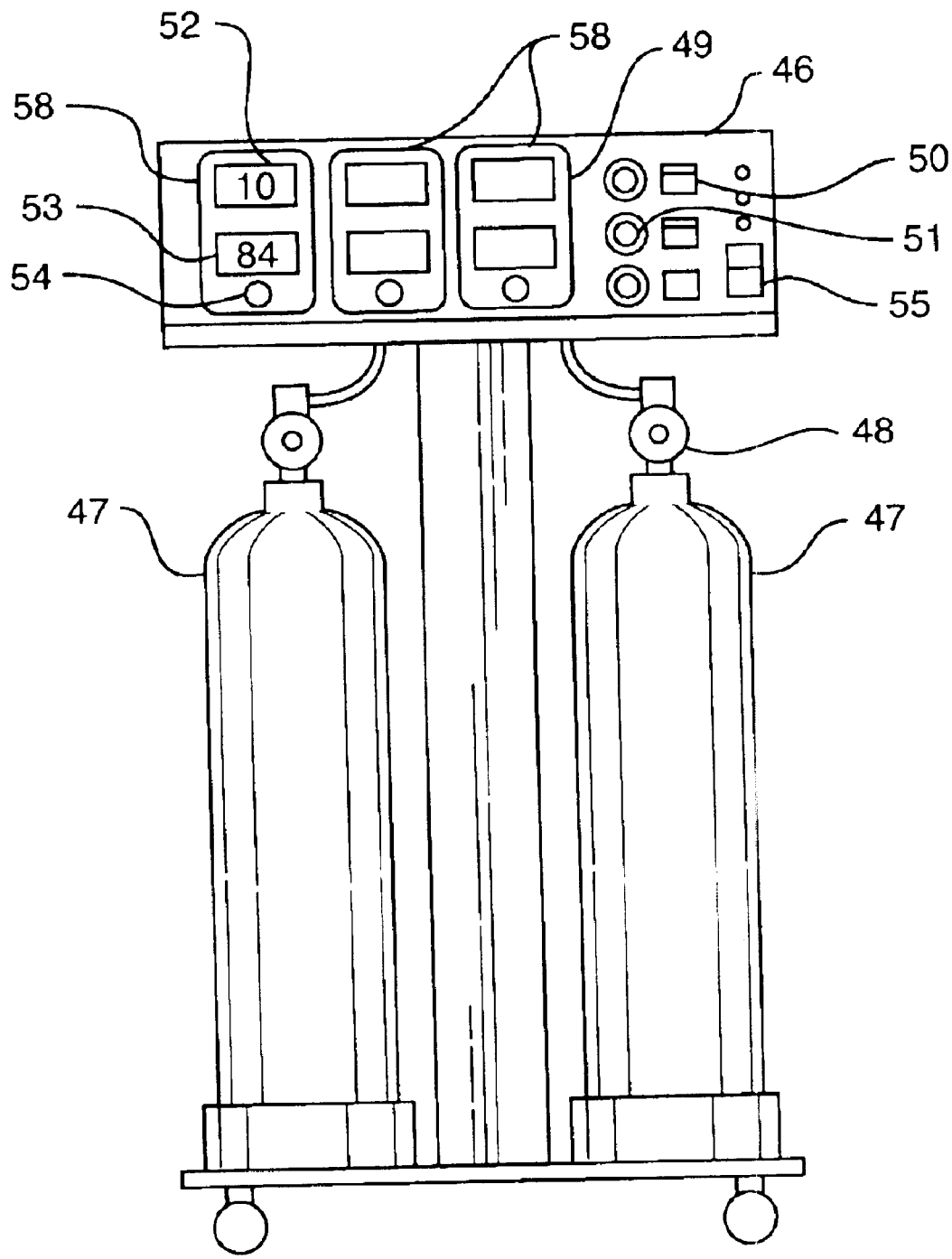
FIGS. 9A & 9B shows the system control console.
Figure 9B:
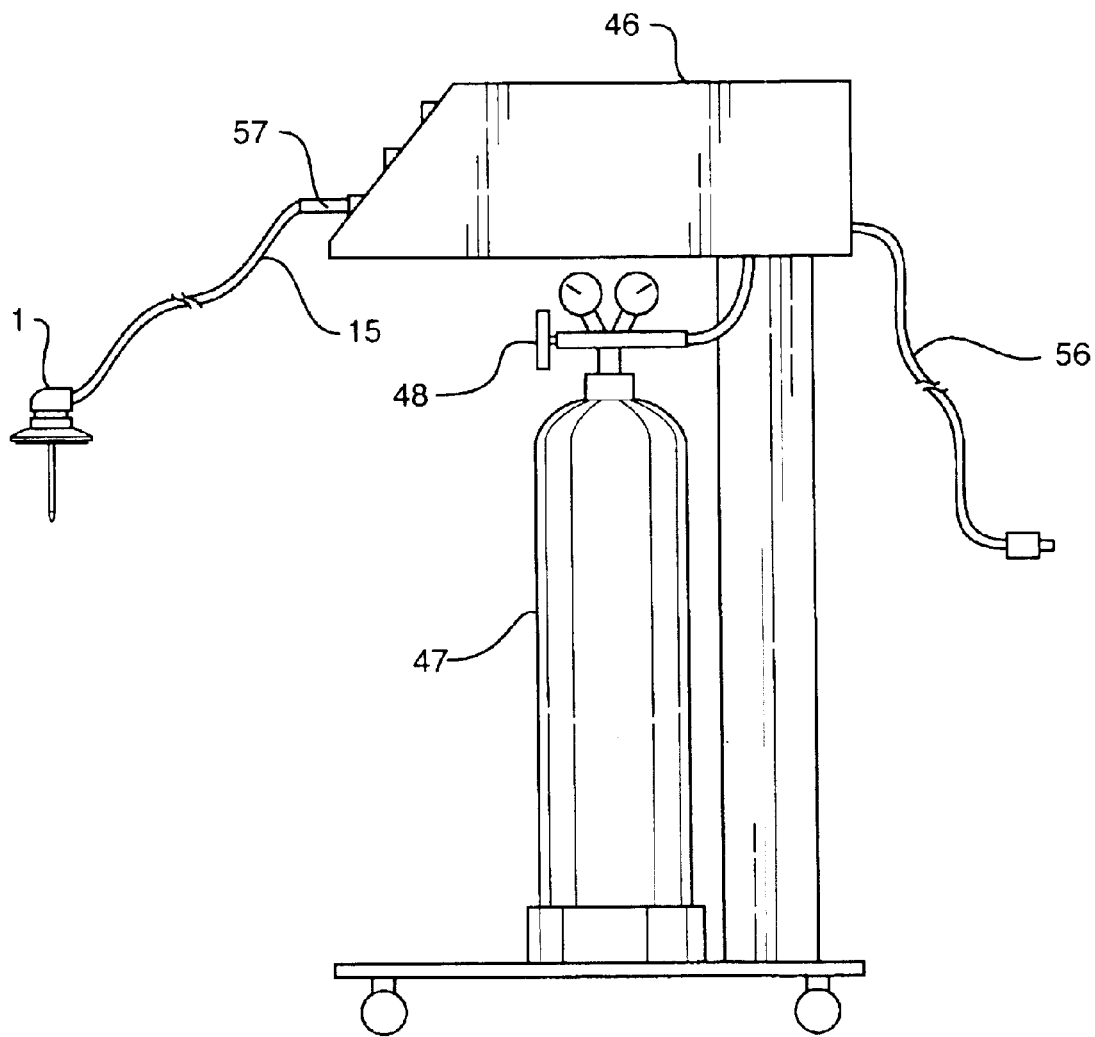

FIG. 9 depicts the system control console. The control console 46, contains a source for cooling gas (argon or nitrogen) in multiple, replaceable tanks 47. The gas tanks are connected to the console using common medical grade pressure regulators 48. The control console 46 has a control panel 49, which provides for a probe tip 4 (FIGS. 1, 2, 3, & 6) temperature display means 52, and a means to display relative cooling power (0% to 100% of maximum heat removal capacity) 53. The control panel has a means to adjust the probe tip 4 temperature setting 54. The control console may be constructed to provide for operation of multiple probes 1 simultaneously by means of multiple display and control channels 58. The control console 46 has means to removably connect the probe umbilical 15 to the control console, where the connection means is by gas plug 57 on the end of the probe umbilical cable 15, and gas plug receptacle 51 mounted on the front of the control panel 49. The control console also provides an electrical connection means for the probe tip thermocouple leads 26 (FIGS. 3, 4, 6 & 8) by the thermocouple receptacle 50 on the control panel 49. The thermocouple leads 8 exits the probe umbilical cable 15 near the gas plug 57 and is terminated by a standard thermocouple connecter plug (not shown).

Figure 10:
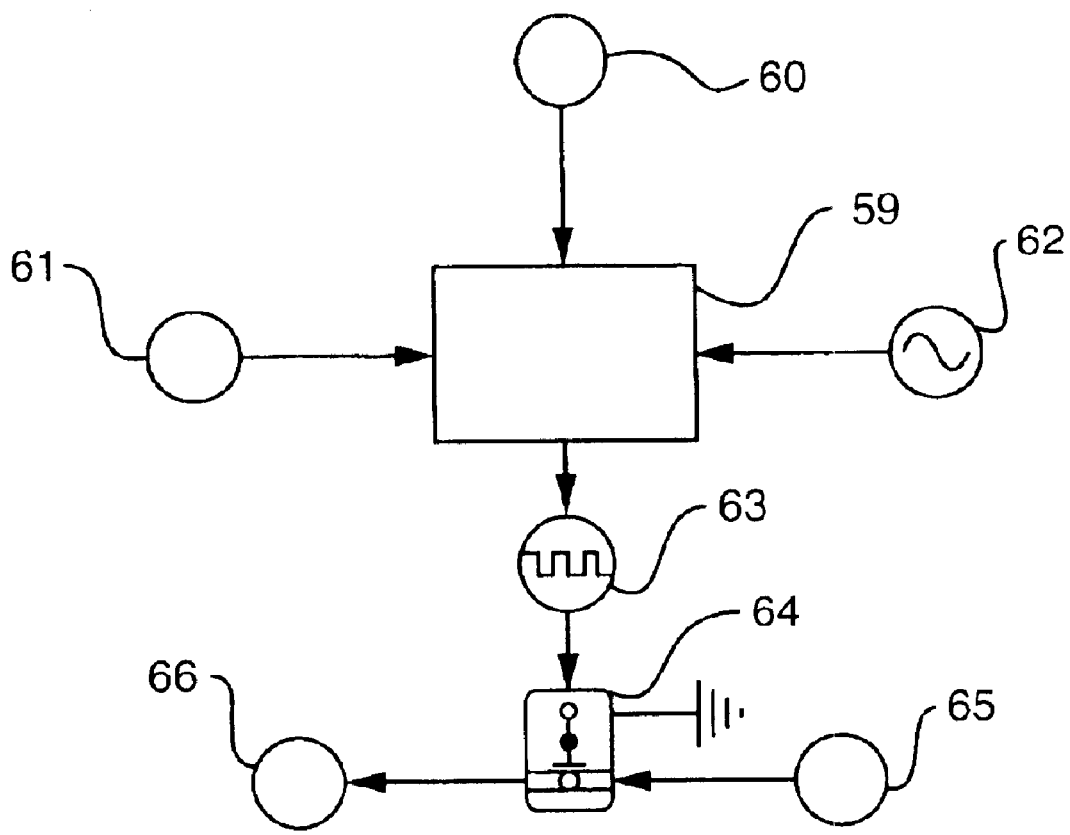
FIG. 10 shows a schematic of the preferred probe tip temperature control means.

FIG. 10 depicts, in schematic form, the preferred method of controlling the temperature at the probe tip 4 (FIGS. 1, 2, 3, 4 & 6). The control console contains electronic circuitry 59 that controls the gas flow from the gas tanks 65 to the probe 66 to maintain an operator set probe tip 4 temperature. Voltage from the probe tip thermocouple 61, and a voltage representative of the operator set temperature 60 are input into the control circuitry 59. The control circuitry produces a modulation waveform that opens and closes the gas solenoid valve 64 according to the gas flow requirements for achieving and maintaining the operator set probe tip 4 temperature. The percentage of time the valve is opened verses the percentage of time the valve is closed defines the relative probe tip 4 cooling power, where when the solenoid valve is open continuously, the probe tip 4 cooling power as at 100% of maximum, and when the solenoid valve closed continuously the probe tip 4 cooling power is at 0% of maximum.

Advantages

From the description above there are a number of advantages my method and apparatus for treating stroke provide:

(a) The therapeutic agent (hypothermia) for treating stroke according to this invention is applied directly to the volume of brain tissue at risk of death and injury from stroke.

(b) The therapeutic agent (hypothermia) for treating stroke according to this invention is limited to the volume of brain tissue at risk of death and injury from stroke.

(c) Lower hypothermic temperatures can be practically achieved in the volume of brain tissue at risk of death and injury from stroke than can be achieved by the methods currently described in the art.

(d) Within the volume of brain tissue at risk of death and injury from stroke, brain tissue with a lower blood perfusion rate is cooled to a lower hypothermic temperature than brain tissue with a higher blood perfusion rate.

(e) Cellular protein migration from an infarcted zone of brain tissue to brain tissue surrounding the infarcted zone may be arrested or retarded.

(f) Hypothermic temperatures can be achieved in the volume of brain tissue at risk of death and injury from stroke faster than with methods described in the art.

(g) Hypothermic temperatures can be maintained longer in the volume of brain tissue at risk of death and injury from stroke than with methods described in the art.

(h) Hypothermic temperatures can be achieved in a large volume of brain tissue at risk of death and injury by means of a single small caliber cooling probe.

(i) The degree of hypothermia in the volume of brain tissue at risk of death and injury from stroke can be adjusted according to the physiological response to hypothermia.

I claim:

1. A method for reducing secondary ischemic brain injury comprising the steps of:

(a) placing a probe into an ischemic region of the brain;

(b) cooling said ischemic region with said probe for a period of time greater than one hour, and less than one month;

(c) removing said probe from said brain.

2. The method of claim 1 wherein said probe is a brain-cooling probe comprising an elongated structure that includes a distal end, and a proximal end, where a cooling means is provided in the vicinity of said distal end, and where a means to fixate said brain-cooling probe to the head is provided in the vicinity of said proximal end.

3. The method of claim 2 wherein said brain-cooling probe includes a means to sense temperature in the vicinity of said distal end.

4. The method of claim 1 wherein said cooling results in at least some portion of said ischemic region being at a temperature below zero degrees centigrade for a period of time greater than one hour, and less than one month.

5. The method of claim 1 wherein said cooling is adjusted according to a physiological response to said cooling where said physiological response is a change in intracranial pressure.

6. The method of claim 1 wherein said cooling is adjusted according to a physiological response to said cooling where said physiological response is a change in patient symptoms.

7. The method of claim 1 wherein said cooling is adjusted according to a physiological response to said cooling where said physiological response is a change in blood perfusion rate within said ischemic region.

8. The method of claim 1 wherein said cooling is adjusted according to a physiological response to cooling where said physiological response is a change in blood chemistry.

9. The method of claim 1 wherein said probe is placed into said ischemic region where said ischemic region comprises brain tissue that has been irreversibly injured.

10. The method of claim 1 wherein said cooling is substantially limited to said ischemic region.

11. An interstitial brain-cooling probe comprising:

(a) an elongated structure which includes a distal end, and a proximal end;

(b) a cooling means located in the vicinity of said distal end;

(c) a means in the vicinity of said proximal end for fixating said interstitial brain-cooling probe to the head, said means of fixating having a means for preventing infection; and (d) a means of connecting said interstitial brain-cooling probe to a source of cooling fluid.

12. The interstitial brain-cooling probe of claim 11 wherein said elongated structure is sized such that said distal end may be placed into an ischemic region of the brain by standard stereotaxic surgical technique.

13. The interstitial brain-cooling probe of claim 11 includes a physiological sensor located in the vicinity of said distal end.

14. The interstitial brain-cooling probe of claim 13 wherein said physiological sensor is a temperature sensor.

15. The interstitial brain-cooling probe of claim 13 wherein said physiological sensor is an ultrasound transducer.

16. The interstitial brain-cooling probe of claim 11 wherein said cooling means is provided by Joule-Thompson effect.

17. The interstitial brain-cooling probe of claim 11 wherein said cooling means is provided by evaporation of liquid refrigerant.

18. The interstitial brain-cooling probe of claim 11 wherein said means of fixating said interstitial brain-cooling probe to the head provides for brain cooling for a period of time greater than one hour, and less than one month.

19. The interstitial brain-cooling probe of claim 18 wherein said means of fixating includes a means of removably fastening said interstitial brain-cooling probe to said head.

20. The interstitial brain-cooling probe of claim 11 wherein said means of connecting said interstitial brain-cooling probe to said source of cooling fluid comprises an umbilical where said umbilical includes at least one cooling fluid conduit.

21. The interstitial brain-cooling probe of claim 20 wherein the axis of said umbilical is approximately perpendicular to the axis of said interstitial brain-cooling probe at the point of connection to said interstitial brain-cooling probe.

22. A system for reducing ischemic brain injury comprising:
   (a) an interstitial brain-cooling probe consisting of an elongated structure with a distal end and a proximal end, where a brain cooling means is provided in the vicinity of said distal end, and where a means of fixating said interstitial brain-cooling probe to a head is provided in the vicinity of said proximal end, said means of fixating having a means for preventing infection, where a means to sense temperature in the vicinity of said distal end is provided by a temperature sensor located in the vicinity of said distal end, and where a means of connecting said interstitial brain-cooling probe to a console is provided by an umbilical, where the umbilical includes a means for supplying cooling fluid from said console to said interstitial brain-cooling probe, and a means of supplying electrical signals from said temperature sensor to said console;
   (b) the console containing a source of cooling fluid, and a means to control a flow of said cooling fluid to said interstitial brain-cooling probe according to signals received from said temperature sensor mounted on said interstitial brain-cooling probe in the vicinity of said distal end;
   whereby said system provides for cooling of an ischemic region of the brain for a period of time greater than one hour, and less than one month.

23. The system of claim 22 wherein the interstitial brain-cooling probe further comprises an ultrasound transducer located in the vicinity of said distal end, the ultrasound transducer configured to detect ice formation at the distal end of the elongated structure.

24. The system of claim 22 wherein the means of fixating the interstitial brain-cooling probe comprises a pad having an antiseptic fluid.

25. An interstitial brain-cooling probe comprising:
   a probe shaft having a distal end and a proximal end;
   a probe housing coupled to the proximal end of the probe shaft, the probe housing configured to couple to a portion of a skull of a head, in proximity to a surgically created opening defined by the skull; and
   a cooling mechanism disposed at the distal end of the probe shaft, the cooling mechanism configured to receive a cooling fluid from a cooling fluid source.

26. The interstitial brain cooling probe of claim 25 wherein the probe housing comprises at least one stationary pod and at least one adjustable pod, the at least one stationary pod and the at least one adjustable pod configured to align the probe housing relative to the skull.

27. The interstitial brain cooling probe of claim 25 wherein the probe shaft comprises an ultrasonic transducer configured to detect ice formation at the distal end of the probe shaft.

28. The interstitial brain cooling probe of claim 25 wherein the probe housing comprises a pad having an antiseptic fluid, the pad configured to orient between the probe housing and the head.

29. A method for treating ischemic stroke comprising:
   surgically creating an opening within a skull of a head;
   placing an interstitial brain-cooling probe within the opening into an infarcted volume of brain tissue, the interstitial cooling probe having a probe shaft having a distal end and a proximal end, a probe housing coupled to the proximal end of the probe shaft, and a cooling mechanism disposed at the distal end of the probe shaft;
   fixing the probe housing of the interstitial brain-cooling probe to the skull in proximity to the surgically created opening; and
   cooling the infarcted volume of brain tissue with the interstitial brain-cooling probe to reduce metabolic activity of tissue surrounding the infarcted volume.

30. The method of claim 29 further comprising placing a pad, having an antiseptic fluid, between the probe housing and the head.

* * * * *